United States Patent [19]

Darling

[11] 4,436,090

[45] Mar. 13, 1984

[54] PISTON ACTUATED, PILOT VALVE OPERATED BREATHING REGULATOR

[76] Inventor: Phillip H. Darling, 38 Meadowgrass, Irvine, Calif. 92714

[21] Appl. No.: 291,998

[22] Filed: Aug. 11, 1981

Related U.S. Application Data

[63] Continuation of Ser. No. 5,158, Jan. 22, 1979, abandoned.

[51] Int. Cl.³ .............................................. A62B 7/00
[52] U.S. Cl. ........................... 128/204.26; 128/205.24; 137/491
[58] Field of Search ...................... 128/204.24, 204.25, 128/204.26, 204.29, 205.11, 205.19, 205.24; 137/491, 492, 489

[56] References Cited

U.S. PATENT DOCUMENTS

| | | | |
|---|---|---|---|
| 2,855,923 | 10/1958 | Kimes et al. | 128/204.26 |
| 2,886,049 | 5/1959 | Holms et al. | 137/491 X |
| 3,076,454 | 2/1963 | Evans et al. | 128/204.26 |
| 3,101,732 | 8/1963 | Dalla Valle | 128/204.26 |
| 3,526,241 | 9/1970 | Veit | 137/489 X |
| 3,688,794 | 9/1972 | Bird et al. | 128/205.24 |
| 3,783,891 | 1/1974 | Christiansen | 128/204.26 |
| 4,054,133 | 10/1977 | Myers | 128/204.26 |
| 4,127,129 | 11/1978 | Cramer | 128/204.29 |
| 4,180,066 | 12/1979 | Milliken et al. | 128/205.24 |

FOREIGN PATENT DOCUMENTS 456066  10/1936  United Kingdom ........... 128/204.26

*Primary Examiner*—Lee S. Cohen
*Attorney, Agent, or Firm*—Knobbe, Martens, Olson & Bear

[57] ABSTRACT

A breathing regulator includes a pressure-responsive piston which acts directly on a valve seat to open a pressurized gas pilot valve during inhalation. The same piston provides an outlet for exhalation. The piston is moved to open the pilot valve by inhalation suction. A one-way valve automatically blocks the exhalation path during inhalation. The outlet for the pressurized gas provides an injector nozzle effect to reduce the effort required to actuate the valve during inhalation. The preferred embodiment of the invention incorporates the regulator in a resuscitator or respirator for medical applications. In this embodiment, a mechanism is included for controlling the amount of inhalation back pressure in the patient's air passages which will close the pressurized gas valve and open the exhaust passage in the regulator. This mechanism includes an adjustable spring-loaded pressure plate on the external side of the piston. The inhalation pressure adjusting mechanism also provides for positive end expiratory pressure. In another embodiment, the basic regulator is adapted for use as a breathing regulator for high altitude aviation. In this embodiment, the invention includes aneroid bellows which close an ambient air inlet when a predetermined altitude is reached, so that breathing is exclusively from a pressurized gas source. The aviation embodiment also provides for pressurized breathing.

74 Claims, 12 Drawing Figures

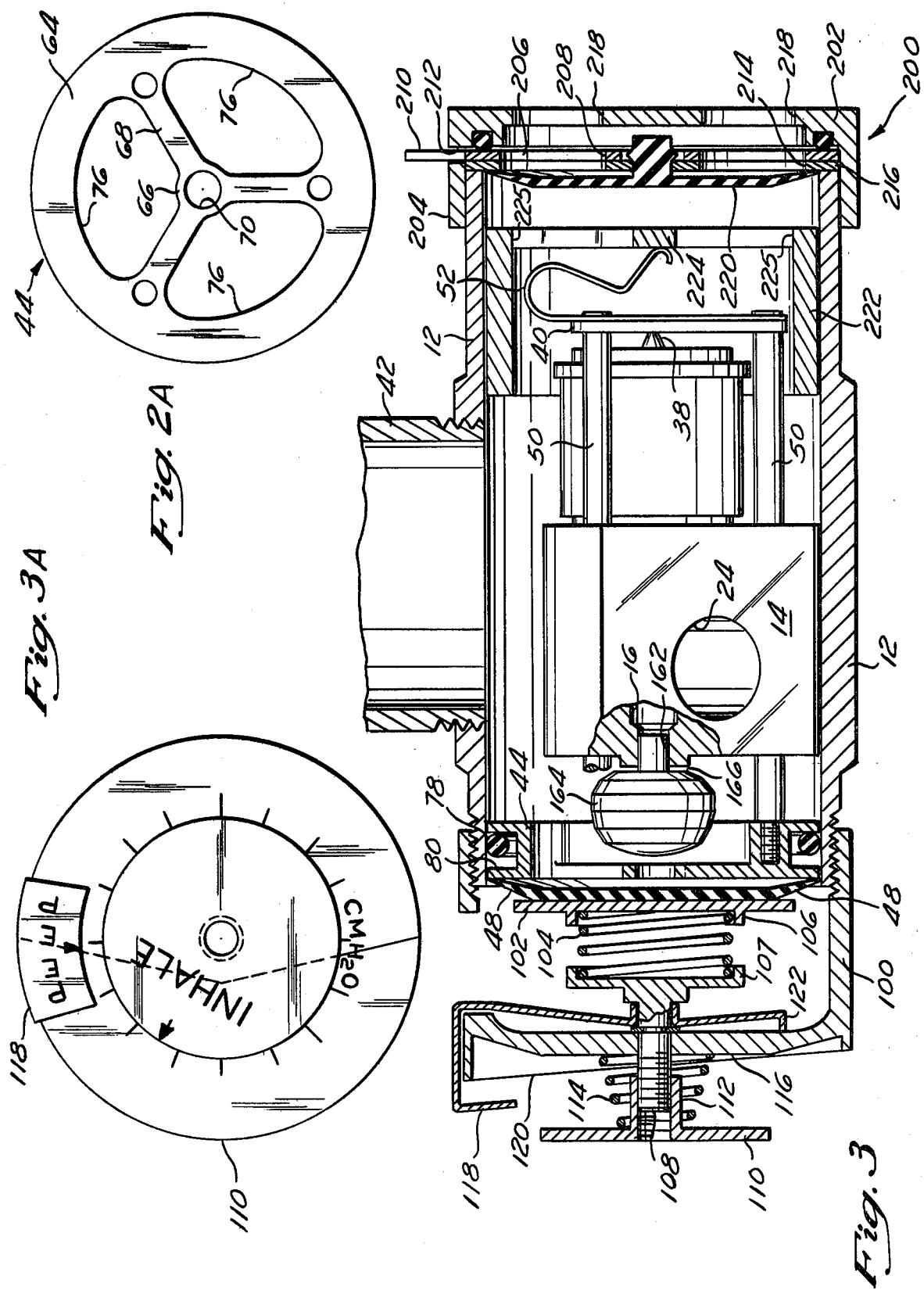

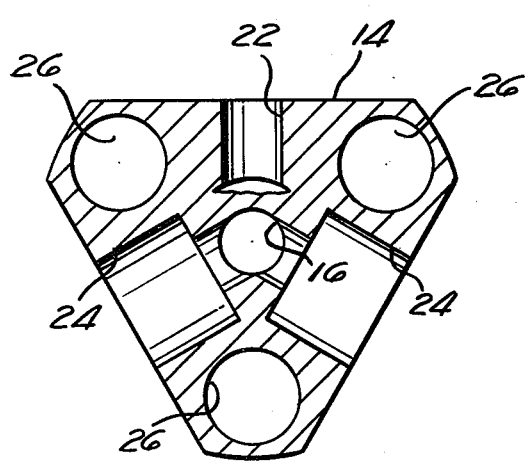
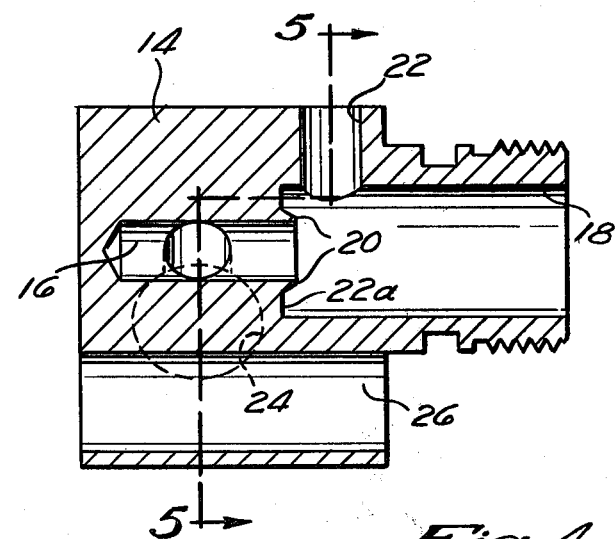
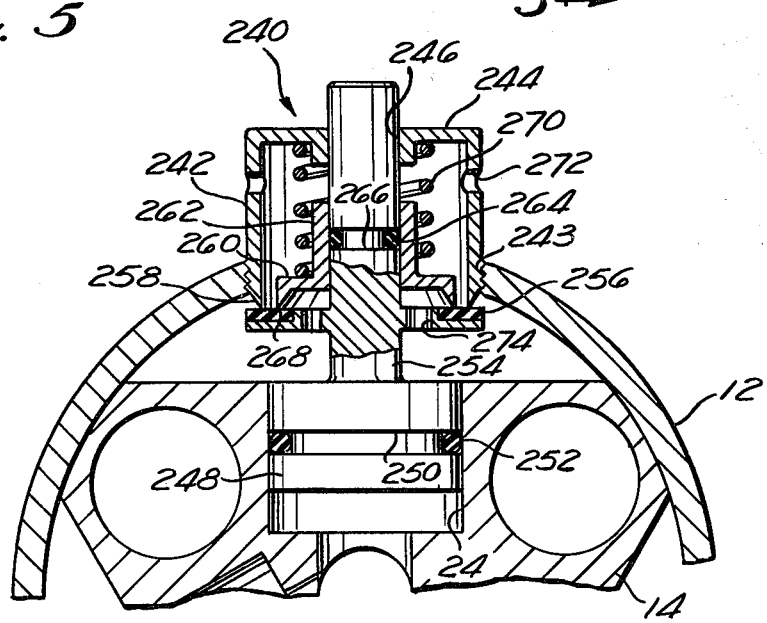
Fig. 5
Fig. 4
Fig. 6

PISTON ACTUATED, PILOT VALVE OPERATED BREATHING REGULATOR

This application is a continuation of application Ser. No. 5,158, filed 1/22/79, now abandoned.

BACKGROUND OF THE INVENTION

This invention relates to the field of breathing regulators and, in particular, it relates to multipurpose breathing regulators incorporating a pilot valve to regulate the flow of pressurized gas.

The use of pilot valves to permit small control forces to actuate the opening and closing of a main valve against large pressure gradients is well known. A pilot valve, by definition, meters a small amount of high pressure fluid through one end of a valve spool having an adequate net cross-sectional area to develop the force on the spool required to hold the main valve closed. Venting the pressure behind the spool allows line pressure to unseat the spool, opening the valve.

Presently, breathing regulators which use pilot valves typically utilize large diaphragms and linkages which provide the force and leverage necessary to control the venting of the valve spool control pressure. Nevertheless, the flow rate is quite often severely limited because of instabilities in valve operation known as "flutter" or "chatter". Moreover, the present pilot valve actuated breathing regulators are frequently delicate, large, and complex, requiring fine adjustment and protection from the operating environment.

Another limitation found in present breathing regulators stems from the need to provide balanced inhalation and exhalation pressures. At present, the breathing regulators used in medical applications accomplish this result by using separate inhalation and exhalation valves which must be separately adjusted to achieve the proper balance.

Specifically, therapeutic medical respirators and resuscitators that provide positive pressure breathing all have separate exhalation valves that must be locked shut during pressurized breathing. Separate mechanical or pneumatic actuators are required to accomplish this result. Furthermore, such respirators that provide adjustable automatic (timed) positive pressure breathing frequently require elaborate casing assemblies to contain the basic valve and its controls, and complex hose assemblies leading to the patient's face mask or tracheal tube. Furthermore, at present, only very large and expensive therapeutic respirators offer positive end expiratory pressure (PEEP). Moreover, the PEEP capability of many such machines is only passive, resisting outflow, but not actively maintaining the set pressure.

Although the use of pilot actuated valving mechanisms is known in scuba and contaminated air respiration systems, the valve mechanisms used in such applications require the use of large diaphragms and complex mechanical linkages which make such mechanisms relatively large and which severely limit their reliability. Furthermore, in contaminated air respiration systems, continuous positive pressure to combat leaks in the system has been provided by utilizing a separate exhaust valve actuated by a heavy spring.

The use of pilot actuated valving mechanisms is also well known in high altitude aviation respiration systems. However, at present such systems lack the negative pressure capability for the protection of an aviator's air passages during explosive decompression. Furthermore, such respiration systems typically require forceful exhalation.

SUMMARY OF THE INVENTION

The basis of the present invention is a breathing regulator valve mechanism in which a pressure responsive piston acts on a valve seat which is integral with it to open a pressurized gas pilot valve during inhalation. The same piston provides an outlet for exhalation. In this basic configuration, which is suitable for use as a scuba diving breathing regulator, the piston is moved to open the pilot valve by the suction of inhalation.

Specifically, pressurized breathable gas is conducted into a first chamber within the valve body. From this chamber, the gas is metered through a bore in a main valve spool to a second chamber which then becomes pressurized. The valve spool is designed so that the surface area exposed to the second chamber is greater than the surface area exposed to the first chamber, so that the valve spool is urged away from the second chamber against a valve seat closing the valve outlet.

The piston provides the single pressure interface between the exterior and interior of the regulator. When suction, as by inhalation, is applied to the interior of the regulator, the pressure on the interior side of the piston is reduced with respect to the externally applied pressure. This pressure differential across the piston causes the piston to move in a first direction. The piston is directly connected to a moveable pilot valve seat, and the movement of the piston in the first direction moves the seat away from the pilot valve outlet so as to open the pilot valve.

The pilot valve inlet is in communication with the second pressurized chamber, so that the opening of the pilot valve permits the gas to escape from this chamber. The depressurization of the second chamber through the pilot valve allows the pressure in the first chamber on the opposite side of the spool to push the main valve spool away from its seat, thereby opening an outlet passage for the pressurized gas to flow into the user's air passages.

The direct opening of the pilot valve by the movement of the pressure responsive piston provides several advantages over prior art breathing regulators which actuate the pilot valve by means of a pressure responsive diaphragm acting through a mechanical linkage. Specifically, the piston provides greater durability and reliability than the easily torn diaphragms of the prior art, since such diaphragms must be relatively thin in order to provide the necessary pressure sensitivity. However, sensitivity comparable to such diaphragms has been retained by (1) using a direct connection between the piston and the pilot valve seat which allows the pilot valve seat to be actuated by the straight-line motion of the piston over a very short distance, and by (2) floating the piston on an O-ring seal which remains substantially stationary during the very short piston travel so as to provide an almost frictionless fitting for the piston.

Moreover, as compared with diaphragm actuated pilot valves, there is virtually no need for fine adjustment of the actuator mechanism. This results both from the lack of linkages between the pilot valve actuator (i.e. the piston) and from the fact that, with a diaphragm, there is a well-defined rest position for the pilot valve actuator, while there is no such rest position with the piston. Thus, with the piston, it is only the distance traveled by the piston which reuslts in pilot valve actuation, while with a diaphragm, it is the initial position of the diaphragm as well as the distance traveled which determines the degree of pilot valve actuation. Therefore, with a diaphragm it is necessary constantly to adjust the linkage to insure the proper positioning of the diaphragm to provide proper pilot valve actuation.

A further advantage achieved by the present invention is the elimination of the previously mentioned problem of valve instability at high gas flow rates. This is due to the unique configuration of the main valve spool and the main valve seat which allows a partial pressure recovery between the spool and the seat when the valve is slightly opened, so that there is no sudden depressurization in this area which would cause the valve spool rapidly to close, then open again, a phenomenon which is known as "chattering" or "fluttering".

An injector nozzle effect produced by the gas outlet slightly reduces the pressure in the interior of the device without the need for the user to maintain a substantial negative pressure during inhalation, thereby making breathing very easy.

At the end of inhalation, the build up of back pressure in the user's air passages is transmitted to the interior of the device, overcoming the slight negative pressure generated by the outlet nozzle, and allowing the pilot valve seat to be closed against the pilot valve by a spring. With the pilot valve closed, the second pressurization chamber repressurizes, forcing the valve spool against its seat so as to close the pressurized gas outlet. The piston is provided with one or more openings sealed by a one-way outlet check valve so that, when the user exhales, his breath passes through these openings and through the check valve to the ambient surroundings. Thus, in the present invention, the piston not only acts as a pilot valve actuator but also as a valve seat for the exhaust or exhalation valve.

Utilization of the piston as the sole pressure responsive interface for controlling both inhalation and exhalation pressure provides an inherent sensitivity of response to the user's inhalation effort and exhalation effort.

This arrangement also allows the basic regulator to be easily adapted for a variety of widely different applications. Specifically, both inspiratory and expiratory pressure can be set by applying various pressurization means to the exterior of the piston. For example, when the regulator is used in scuba applications, inspiratory and expiratory pressure is set by the pressure of the water against the piston. When the regulator is used as a medical resuscitator or respirator, a controllable pressure plate may be applied against the exterior surface of the piston to provide controllable intermittent positive pressure breathing as well as controllable active positive end expiratory pressure. When the regulator is used in high altitude breathing applications, an altitude responsive aneroid bellows may be used to provide the desired pressurization against the piston.

With specific reference to the use of the regulator as a medical resuscitator or respirator a pressure plate is provided on the exterior side of the piston as previously mentioned. Manual or auomatic controls are provided for adjusting the pressure applied against the piston through the pressure plate so as to bias the piston in its first direction with a predetermined pressure. With the piston biased in its first direction, the pilot valve is opened as previously described, allowing pressurized gas to flow into the patient's lungs. Only when inspiratory pressure in the patient's air passages is sufficient to overcome the pressure applied by the pressure plate against the piston will the piston be urged in the opposite direction so as to close the pilot valve, thereby closing the pressurized gas valve and opening the exhalation passageway through the piston. In this manner, the regulator may be used as a resuscitator with intermittent positive pressure breathing (IPPB).

The same control acting through the same pressure plate can be used to achieve active positive end expiratory pressure (PEEP). The controls can be manipulated to maintain a residual pressure on the piston pressure plate. The patient can then exhale until the pressure in his air passages equals this residual pressure. PEEP can be provided either intermittently or continuously. The PEEP control actively maintains the set pressure so that, if the pressure in the regulator falls below the pressure which is set, the pilot valve is opened to maintain the set pressure.

Thus, a significant advantage of the present invention is the use of a single control mechanism to adjust the external pressurization on the piston to achieve both IPPB and active PEEP. In addition, the same control can be used for IPPB override pressure.

The resuscitator/respirator embodiment of the invention also incorporates means for vacuum assisted exhalation and for the dilution of pressurized oxygen with external ambient air. This embodiment is further provided with an overpressure relief valve and a safety vent which prevents suffocation should the oxygen supply become depleted. Moreover, the simple but rugged structure of the device allows it to be flushed out and autoclaved for cleaning and sterilization without fear of damage. Furthermore, all orifices in the valve mechanism are spring loaded shut when oxygen or other pressurized gas is not flowing, so that the mechanism is protected from dust and contamination as well as from clogging due to, for example, the patient's regurgitation.

As previously mentioned, the regulator is easily adapted for use as a high altitude aviation breathing regulator. In this embodiment the device has an air vent through which the user breathes ambient air at low altitude. As external pressure decreases with increasing altitude, an aneroid bellows gradually seals the vent, Finally, at a predetermined altitude, the bellows completely closes the vent so that the user's inhalation actuates the pilot valve as previously described with regard to the basic regulator. Pressurized breathing in this embodiment is provided by additional aneroid bellows which are responsive to both the pressure at the valve outlet and the external ambient air pressure to pressurize the external side of the piston so that it is biased by a predetermined pressure to its pilot valve opening position. Thus, the pilot valve, and therefore the main valve, will remain open until the inspiratory pressure within the user's air passages reaches this predetermined level. At this point the pilot valve, and therefore the main valve, will be closed as previously described, and the user will be allowed to exhale through the piston openings by free flow to ambient pressure. This is analogous to IPPB operation at altitude and offers a distinct advantage over prior art high altitude breathing regulators by allowing free flow exhalation to ambient pressure inasmuch as present systems require forceful exhalation to open separate exhalation valves.

As compared with present high altitude breathing systems the present invention offers a small, light weight, mask-mounted unit, as opposed to present large, panel-mounted controls. Since all breathing controls are mask-mounted, the bail out oxygen supply could be considerably reduced, since it would not have to be a continuous flow system as at present.

From the foregoing summary, it will be readily appreciated that the design of the present invention is not only readily adapted to a multitude of uses, but is also surprisingly simple with very few moving parts. Consequently, it can be made very compact and light weight, while at the same time having a high degree of durability and reliability with minimal need for adjustment. These advantages and many others will be more clearly seen in the detailed description of the invention which follows.

BRIEF DESCRIPTION OF THE DRAWINGS

FIG. 2A is an elevation view of the piston used in the present invention;

FIG. 3 is a cross-sectional view of the resuscitator embodiment of the present invention;

FIG. 3A is a diagramatic view of the manual controls of the resuscitator shown in FIG. 3;

FIG. 4 is an enlarged cross-sectional view of the valve body illustrated in FIG. 2;

FIG. 5 is a cross-sectional view taken along line 5—5 of FIG. 4;

FIG. 6 is a detailed cross-sectional view of a safety mechanism which is advantageously used with the resuscitator shown in FIG. 3;

DETAILED DESCRIPTION OF THE INVENTION

The Basic Regulator (Scuba Embodiment)

Figure 1:
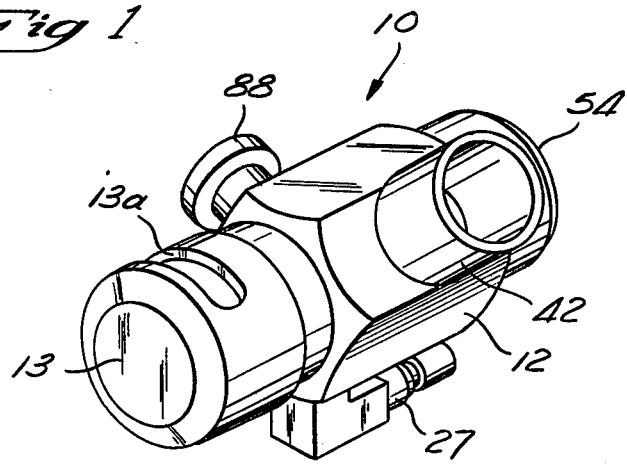
FIG. 1 is a front perspective view of a basic breathing regulator constructed in accordance with the preferred invention.
Figure 2:
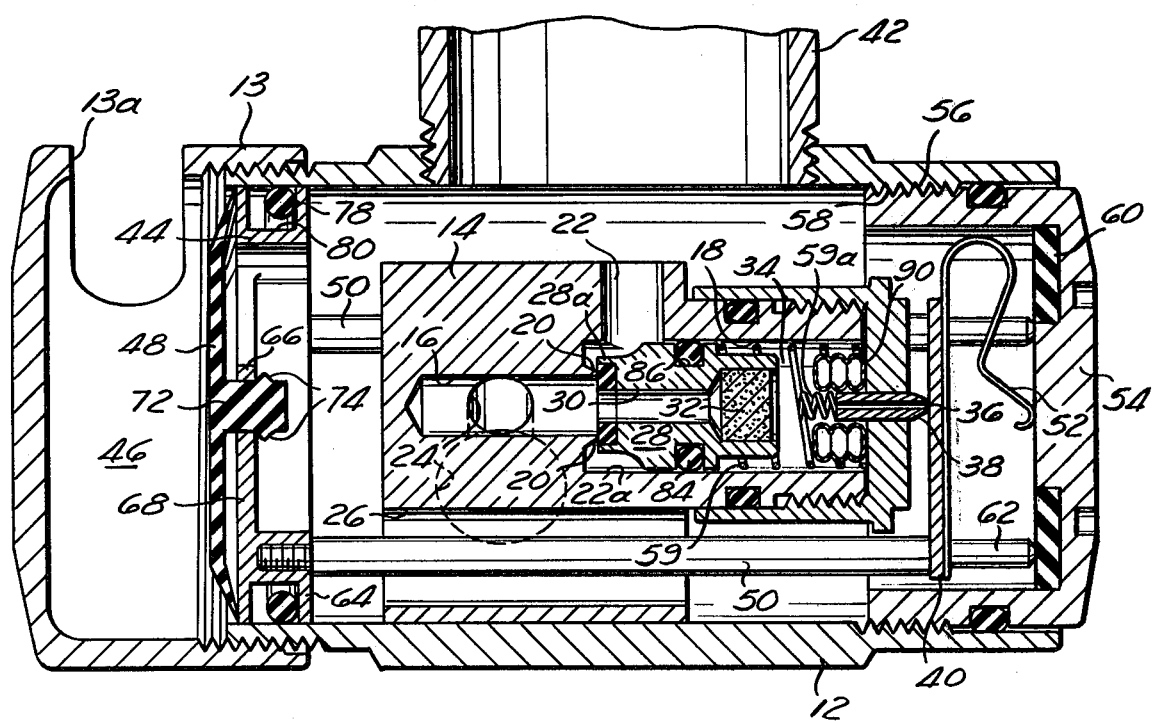
FIG. 2 is a cross-sectional view of the basic breathing regulator of FIG. 1 constructed in accordance with the present invention.

The basic breathing regulator which is the heart of the present invention is illustrated best in FIGS. 1 and 2. This is the embodiment most advantageously used for scuba diving applications.

As shown, a breathing regulator 10 comprises a housing 12, typically made of a corrosion resistant metal such as stainless steel or brass, with a front cap 13 having an opening 13a to ambient. The housing 12 contains a valve body 14, preferably of brass or a similar material. As best shown in FIGS. 4 and 5, the valve body 14 is essentially triangular in cross section with flattened or broadly arcuate corners. The front part of the body 14 is bored out to provide a front or first pressurization chamber 16 which extends rearwardly through the body, opening into a valve spool bore 18. Around the periphery of the front pressurization chamber opening there is formed a lip or ridge which provides a valve spool seat 20. A pressurized gas outlet 22 extends from the valve spool bore 18 to the exterior of the valve body. As best shown in FIG. 5, one or more pressurized gas inlets 24 extend from the first or front pressurization chamber 16 to the exterior of the valve body 14. The valve body 14 is bored through longitudinally at each corner to provide three connecting rod journals 26. As shown, the valve body 14 has two gas inlets 24 and one gas outlet 22. By either lengthening the valve body or by providing it with more than three faces, additional gas inlets and outlets may be provided.

Referring again to FIGS. 1 and 2, pressurized gas, such as oxygen or air (which is typically pressurized to between 50 and 200 pounds per square inch above ambient) is conducted into the gas inlets 24 through a pressurized gas line fitting 27, and into the front pressurization chamber 16. The gas pressurizes the chamber 16 and passes through a main valve spool 28 through an axial bore or passageway 30. The gas exits the opposite end of the spool 28 through a porous, sintered metal (preferably bronze) filter plug 32 and enters a second or rear pressurization chamber 34. The plug 32 serves the dual purpose of filtering particulate contaminants from the pressurized gas, while metering the flow of gas from the bore 30 into the rear pressurization chamber 34 at a rate which is less than the venting rate of an axial pilot valve passageway or orifice 36 in a pilot valve body 38, the passage 36 communicating with the rear pressurization chamber 34. Thus, the rate of flow of gas into the chamber 34 through the plug 32 must be substantially less than the rate of flow out of the chamber so that the opening of the pilot orifice 36 can quickly reduce the pressure in the chamber 34. Alternatively, the plug 32 can be replaced by a restricted orifice having a significantly smaller diameter than the pilot passage or orifice 36 with or without a larger flow area filter plug between it and the bore 30.

In the initial state of the valve mechanism, the pilot valve member 38 seats against a pilot orifice closure plate 40 which closes the end of the pilot passageway or orifice 36 opposite the pressurization chamber 34. Thus, as gas enters the rear pressurization chamber 34, this chamber becomes pressurized.

The main valve spool 28 is designed so that the surface area of the surface facing the second or rear pressurization chamber 34 is greater than the surface area of the surface facing the front pressurization chamber 16. Accordingly, as gas passes through the bore 30, the rear pressurization chamber 34 becomes pressurized, and as the pressure in the rear pressurization chamber 34 approaches that in the front pressurization chamber 16, the force exerted against the surface facing the rear chamber will exceed the force exerted against the surface facing the front chamber, due to the greater area of the rear facing surface as compared with the front facing surface (the force equaling the product of the pressure and the surface area). This force differential across the spool 28 will cause the valve spool to be urged to the left (as shown in FIG. 1), until it is seated against the valve spool seat 20, thereby closing the pressurized gas outlet 22.

When the user of the regulator applies suction to the interior of the regulator by inhaling through an outlet chamber or mouthpiece 42, the pressure in the interior of the regulator is reduced with respect to the pressure on the exterior. This sets up a pressure differential across an apertured piston 44, the outer surface of which is sealed from a chamber 46 by a reislient, one-way outlet check valve 48. The chamber 46 is defined by the check valve 48 and the end cap 13, and communicates with the ambient environment through the opening 13a. The pressure differential between the chamber 46 and the interior of the regulator across the piston 44 causes the piston 44 to be urged to the right as shown in FIG. 2. The piston 44 is directly connected to the pilot valve closure plate 40 by means of three connecting rods 50 (only two of which are shown in FIG. 2) which are journaled in the connecting rod journals 26 through the valve body 14. Thus, when the piston 44 is moved to the right, it urges the pilot valve closure plate 40 away from the pilot valve body 38 against the force of a weak spring 52 which bears against the interior surface of an end cap 54. As the closure plate 40 is moved away from the pilot valve member 38, the pilot valve passageway 36 is opened. When the passage 36 is opened, gas from the chamber 34 escapes through it, thereby depressurizing the chamber 34. The depressurization of the rear chamber 34 allows the pressure in the front pressurization chamber 16 to exert a greater force on the front facing surface of the spool 28 than is exerted on the rear facing surface, to urge the main valve spool ∞ to the right and away from the valve spool seat 20, thereby opening the gas outlet 22. The outlet 22 opens into the user's mouthpiece 42, allowing the pressurized gas to enter the user's air passages.

As shown in FIG. 2, the regulator is shown in a locked position, which is suitable for shipping. The end cap 54 is provided with threads 56 so that it may be screwed in or out of threaded portion 58 of the housing 12. In FIG. 2, the end cap 54 is shown screwed all the way into the housing so that an annular pad 60 around the interior of the end cap 54 bears against extensions 62 of the connecting rods 50 and the closure plate 40 is locked against the orifice 36. When the end cap 54 is screwed out slightly to the right, the plate 40 is unlocked. As the cap 54 is unscrewed further to the right, the pressure on the spring 52 is relieved, so that less force on the piston 44 is required to overcome the pressure of the spring 52 against the closure plate 40 to open the pilot passage 36. Thus, as the cap 54 is unscrewed, less and less forceful inhalation is required to open the pilot valve and actuate the main valve spool 28 to supply the user with pressurized gas. In this manner, the cap 54 may be used to adjust the level of inhalation effort necessary to actuate the valving mechanism. Inhalation effort (suction) may be adjusted to as low as one or two cm $H_2O$ or less.

The main valve spool 28 is designed so that it partially occludes the outlet 22 when the pilot valve is closed. This partial occulsion is provided by the full diameter portion of the spool 28 which extends across approximately half of outlet 22 in the closed position. When the valve begins to open and the main valve spool 28 lifts off of the valve seat 20, there is a marked drop in pressure as the pressurized gas accelerates through the spool passage 30. The partial occlusion of the outlet passage 22 provides for a pressure recovery at the left side of the valve spool 28, and the main valve opens regardless of the flow rate through the passage 30. Without such a means of pressure recovery, the pressure drop at the left end of the spool 28 would result in a sudden decrease in the force against the left or front facing surface of the spool 28 which, in turn, would cause the valve rapidly to close as soon as it opens, and then open again (a phenomenon known as "chatter" or "flutter") at anything greater than moderate gas flow rates. Once the main valve spool 28 fully opens (that is, at its right-most extreme in FIG. 2), the outlet passage 22 is no longer occluded and flow therethrough into the mouthpiece 42 is unimpeded.

A weak coil spring 59 located around the wall of the valve bore 18 urges the spool 28 shut against the valve seat 20 when no pressurized gas is flowing. A small diameter coil spring 29a seated on the pilot body 38 in the chamber 34 compensates for the dynamic pressure exerted against the left side of the spool 28 by the escape of pressurized gas between the spool 28 and the valve seat 20, so that the movement of the spool 28 can be controlled by the opening of the pilot orifice 36.

The pressurized gas outlet 22 is configured so as to provide a slight injector nozzle effect as the gas passes through it. The injector nozzle effect can be adjusted to slightly reduce the pressure in the interior of the regulator, thereby eliminating the need for the user to maintain a constant negative pressure during inhalation. The result is to make breathing very easy.

One or more additional outlets (not shown) similar to the outlet 22 but directed to the regulator and located to the right of the outlet 22 may be provided. These outlets would be uncovered as the spool 28 opens the valve, thereby pressurizing the interior of the valve and balancing the injection nozzle effect of the outlet 22 which tends to suck the valve fully open. By controllably repressurizing the chamber 34 to the left of the spool 28 through the use of these additional outlets, it is possible to eliminate the springs 59 and 59a.

At the end of inhalation, the build up of back pressure in the user's air passages is transmitted to the interior of the regulator, overcoming the slight negative pressure generated by the injector nozzle effect of the gas outlet 22, and thereby allowing the spring 52 to push the pilot orifice closure plate 40 to the left as shown in FIG. 1, closing the pilot passage or orifice 36. The rear or second pressurization chamber 34 once again becomes pressurized due to the gas passing through the passage 30 of the main valve spool 28. This pressurization will continue until the force on the right side of the valve spool 28 is greater than the force on the left side (due to the greater surface area on the right side) so that the valve spool 28 is pushed to the left until it seats against the valve spool seat 20, closing the gas outlet 22.

As shown most clearly in FIG. 2A, the piston 44 is roughly in the configuration of a spoked wheel with a peripheral rim 64 connected to a central hub 66 by plural spokes 68. The hub 66 is provided with a central aperture 70. As shown in FIG. 2, the resilient outlet valve 48 has a resilient cylindrical central neck 72 which is inserted through the hub aperture 70 thereby attaching the valve 48 to the piston 44. The neck 72 has a peripheral rim 74 which bears against the hub 66. The piston 44 is provided with outlet openings 76 defined by the rim 64, the spokes 68, and the hub 66.

When the user exhales, his breath passes through the mouthpiece 42 into the interior of the device and through openings 76 in the piston 44. The outlet check valve 48 allows the exhaled breath to pass into the chamber 46 and thence to the exterior environment. The valve 48 thus has the dual purpose of acting as a pressure responsive pressure plate for moving the piston which actuates the pilot valve, while also serving as an exhalation outlet check valve.

If the regulator 10 is out of the user's mouth, while he is under water, excess water pressure in the chamber 46 might be expected to force the piston 44 to the right and cause free flow of the valve mechanism. This is a typical problem with conventional scuba diving breathing regulators. However, in the present invention, this problem is substantially eliminated. The simple construction of the present invention allows it to be very compactly made, and the small size precludes the build-up of a substantial water pressure head in the chamber 46 before the interior of the device floods via the mouthpiece 42. Secondly, shocks cannot be transmitted to the piston 44 since the chamber 46 opens in the same direction as the mouthpiece 42, and pressure surges or shocks will be equally transmitted to both sides of the piston 44. In conventional regulators, this is not usually the case. Furthermore, such regulators include a purge button which is typically connected to a diaphragm which opens the gas valve. Consequently, accidental shocks to the purge button cause free flow unless the valve spring is set tightly enough to shut off the valve as it is activated. Accordingly, it is necessary that the valve have a relatively hard breathing operation to prevent free flow under normal conditions when the regulator is not in use. By eliminating this problem, the regulator of the present invention can be made extremely easy breathing while at the same time substantially improving the safety factor by minimizing the probability of free flow.

It will be readily appreciated that the piston 44 is the only pressure-responsive interface between the interior and the exterior of the regulator for controlling both inhalation and exhalation pressure, thus providing an inherent sensitivity of response to the user's inhalation effort and exhalation effort without the need for separate adjustment of separate inhalation and exhalation valves.

Simplicity of operation, reliability, and durability of the device are enhanced by the direct connection between the pilot actuator (i.e., the piston 44) and the pilot orifice closure plate 40, which eliminates the complex linkages of the prior art, which require frequent adjustment. Moreover, this direct connection permits straight line motion of all moving parts, so that all motion is characterized by extreme economy of movement. For example, the closure plate is moved only about 0.1 mm (0.004") from its closed to open positions. Thus, the piston need only move this same distance, because of the direct linkage. This economy of movement minimizes friction, and therefore wear and breathing effort are likewise minimized.

The use of a piston, rather than the diaphragm of the prior art, to actuate the valve results in increased durability, as the diaphragms typically used must be relatively thin to afford the necessary pressure sensitivity. Such a high degree of sensitivity has been retained in the present invention by an essentially frictionless fitting for the piston 44 in the housing 12.

This fitting is provided by an O-ring 78 loosely placed in a peripheral groove 80 in the rim 64 of the piston 44. The O-ring 78 has a slightly larger outside diameter than the inside diameter of the housing 12, while having a cross-sectional thickness which is narrower than the width of the groove 80. Thus, the O-ring fits snugly against the wall of the housing to provide a stationary seal, while the piston 44 is allowed to move, substantially without friction, a distance equal to the difference in widths between the O-ring 78 and the groove 80. This distance need only be about 0.1 mm, as previously mentioned, to effect valve actuation. Thus, the piston is allowed to move the necessary distance substantially without friction by "floating" on a stationary O-ring seal.

It will be further appreciated that a piston, unlike a diaphragm, does not have a fixed "rest position". That is, a piston can actuate the valve mechanism merely by traveling a certain distance between any two positions, while a diaphragm must travel a certain distance from a fixed rest position. Thus, a diaphragm valve-actuator requires a degree of fine adjustment to ensure proper positioning for achieving the desired valve actuation. This adjustment is, of course, unnecessary with a piston.

A second O-ring 84 is located in an annular groove 86 around the exterior of the valve spool 28 to provide an effective seal between the spool and the walls of the spool bore 18.

A purge valve 88 connects the front pressurization chamber 16 to the interior of the regulator. Actuation of this valve directs a purge flow of pressurized gas into the regulator interior to blow water out of the mouthpiece 42. The pressurization of the interior of the regulator by this flow of gas prevents the valve mechanism for being actuated, so that purge-induced free-flow is rendered impossible. The purge valve can also be used as an emergency, mannually-operated breathing valve should the main valve mechanism fail. In such an event, the outlet check valve 48 would prevent the overpressurization of the diver's lungs.

As the diver's depth increases, the increasing ambient pressure results in the increased density of the pressurized gas being delivered to the valve 28. Accordingly, the valve 28 must open wider, with increasing depth to deliver a constant volume per unit time of air or oxygen to the diver so as to compensate for the lower flow rates due to increased gas density. To enable the valve 28 to open wider in response to increased depth, an annular aneroid bellows 90 is provided in the rear pressurization chamber 34, surrounding the pilot passage body 38 in confronting relationship to the plug 32. The bellows 90 is responsive to the external ambient pressure, via the pressurized breathing gas which is maintained at a set pressure above ambient, contracting with increased pressure and expanding with decreased pressure. Thus, as depth increases, the bellows 90 contracts, allowing the valve spool 28 to travel farther to the right before the plug 32 abuts against the bellows 90, thereby allowing more of the gas outlet 22 to be unobstructed to the passage of pressurized gas.

Medical Resuscitator/Respirator Embodiment

The scuba diving breathing regulator described above will function in air as a sensitive, user-demand regulator. The basic regulator is the heart of a versatile, operator-actuated respiration valve when modified as described hereinafter.

Referring to FIG. 3, an exhaust cap 100 carrying the manually operated controls is fitted to the piston side of the housing 12. The piston 44 and the rest of the basic regulator are the same as described above, except for the outlet arrangement modifications which will presently be discussed.

As shown in FIG. 3, a rigid pressure plate 102 is placed against the outlet valve 48. One end of a coil spring 104 is attached to an annular seat 106 located on the pressure plate 102 while the other end of the spring 104 is attached to a circular, movable spring seat 107. Extending outwardly from the spring seat 107 is a shaft or plunger 108, the terminal end of which is threaded. An inhalation control dial 110 having an internally threaded shaft 112 is screwed onto the threaded end of the plunger 108. A second coil spring 114 surrounds shafts 108 and 112 and seats against the underside of the inhalation control dial 110 and against an exhaust cap top 116.

As previously mentioned, the control dial 110 is screwed onto the shaft or plunger 108. The farther the dial 110 is screwed onto the plunger 108, the smaller the distance it can travel before the base of the shaft 112 abuts against the exhaust cap top 116. When the operator pushes the control dial 110 to the right, the plunger 108 and the spring seat 107 are pushed to the right, causing the annular spring seat 107 to compress the spring 104. Thus, the distance which the plunger 108 is moved to the right determines how much the spring 104 is compressed. Compression of the spring 104 causes a force to be applied against the piston 44 through the pressure plate 102 and the outlet valve 48. This force on the piston moves the piston to the right thereby actuating the valve mechanism as previously described to allow pressurized gas to enter the patient's air passages. The pressure within the patient's air passages is transmitted to the interior of the regulator, and when this pressure equals the pressure applied by the spring 104 to the piston 44, the piston will overcome the spring's bias so as to be moved to the left, thereby closing the pressurized gas outlet 22 in the previously described manner. In this manner, the inhalation control dial 110 controls the inspiratory pressure so as to achieve intermittent positive pressure breathing (IPPB). It will be noted that the pressure plate 102 not only controls the inspiratory pressure, but simultaneously closes the exhaust passage by pressing the outlet valve 48 against the piston 44, thereby sealing the exhaust openings 76. When the inhalation control dial 110 is released at the end of inspiration, the patient exhales passively to ambient through the piston apertures 76 and the check valve 48.

A positive end expiratory pressure (PEEP) control 118 is provided around the periphery of the exhaust cap top 116. If PEEP is desired, the PEEP control 118 is depressed as the inhale control dial 110 is released. The PEEP control 118 depresses the plunger 108 less than the inhalation control 110 so as to maintain a residual pressure on the pressure plae 102. The patient can then exhale until the pressure in his air passages falls to the pressure exerted on the pressure plate 102 by the spring 104. The depression of the PEEP control 118 is controlled by the position to which it is rotated above a sloped rim 120 on the exhaust cap top 116. In the embodiment shown, the PEEP control 118 pivots about a terminal pivot point 122. Other arrangements are, of course, possible and are within the scope of this invention.

When the controls 110 and 118 are not in use, the pressure plate 102 is drawn out of the way by the coil spring 114. The device then functions as a simple demand regulator as in the basic embodiment previously described.

It will be appreciated that the extreme simplicity of the controls follows from the fact that exhalation is through the inhalation piston 44. The pressure exerted by the pressure plate 102 is therefore applied equally to the exhalation valve 48 and the inhalation piston 44, producing the proper respiratory pressure pattern with only two controls coupled to one spring.

Figure 8:
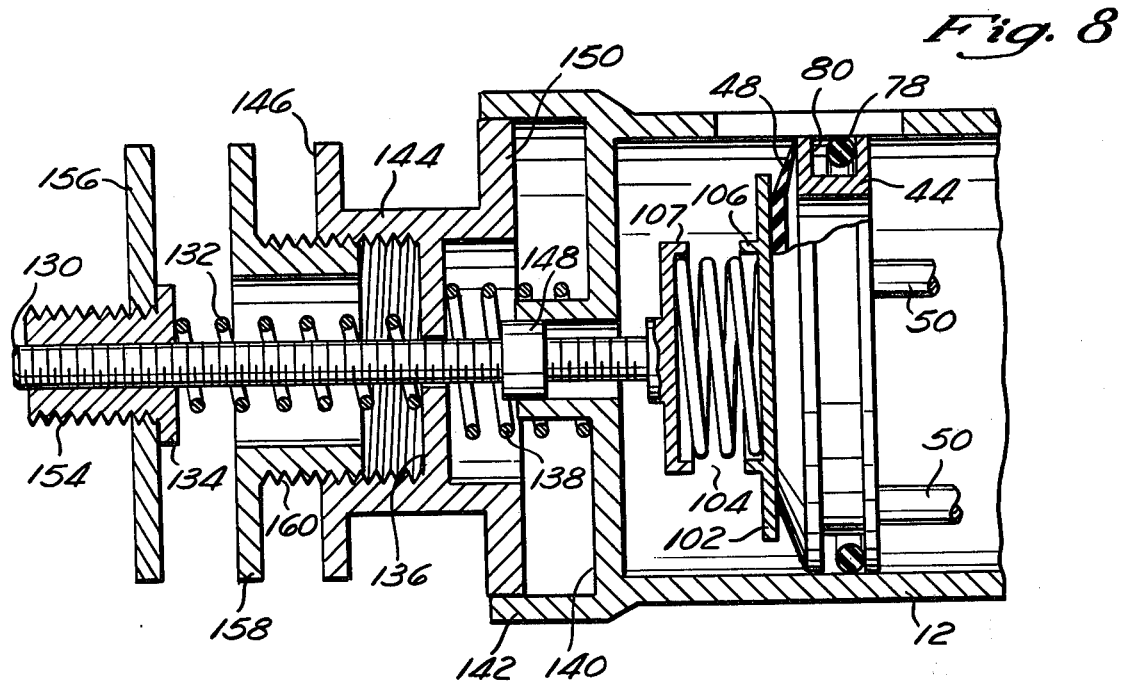
FIG. 8 is a cross-sectional view of an alternative form for the manual controls of the resuscitator embodiment illustrated in FIG. 3.

FIG. 8 shows another embodiment of the resuscitator or respirator controls. A shaft 130 is connected at one end to the circular spring seat 107. A first coil spring 132 surrounds the left-hand portion of the shaft 130 and is seated between spring seats 134 and 136. A second coil spring 138 surrounds the right-hand portion of the shaft 130 and is seated between the spring seat 136 and a recessed surface 140 of an end cap 142. The spring seats 134 and 136 fit snugly against the shaft 130 so that any movement of the spring seats 134 and 136 effects a movement of the shaft. When unactivated, as shown, the whole control assembly is pushed to the left by the springs 132 and 138 bearing against the spring seats 134 and 136, respectively. With the controls in the left-most position as shown, pressure is not applied to the pressure plate 102, thereby permitting unrestricted exhalation to ambient pressure.

A PEEP control lever 144 is connected to the spring seat 136 and has an annular lip or handle 146. When depressed by the operator, the PEEP control lever 144 pushes the shaft 130 to the right, bearing on a nut 148 which is threaded onto the inner end of the shaft 130. PEEP pressure is determined by the degree to which the shaft 130 has been moved to the right by the PEEP control lever 144 when an annular flange 150 at the right end of the lever 144 makes contact with the surface 140 of the end cap 142. The position of the nut 148 controls the amount of movement of the shaft 130. In the configuration shown, the nut 148 is preset and is not readily adjustable, but it will be appreciated that it can be easily made adjustable. It may also be desirable to provide means for locking the PEEP control 144 against the top cap 142 by a detente mechanism (not shown) for continuous PEEP.

Threaded to the shaft 130 and integral with the spring seat 134 is a cylindrical threaded fitting 154. Threaded around the periphery of the fitting 154 proximate the spring fitting 134 is an annular IPPB control 156. When pushed to the right as viewed in FIG. 8, the IPPB control 156 moves the shaft 130 to the right via the fitting 154. The IPPB pressure is set by a ring 158 having a threaded neck 160 which screws into the PEEP control lever 144. As the IPPB control 156 is pushed to the right it contacts the ring 158, thereby engaging the PEEP control lever 144. This rightward movement continues until the PEEP control flange 150 contacts the cap surface 140. Thus, the amount that the IPPB pressure control ring 158 is screwed into the PEEP control lever 144 determines how far the shaft 130 may be moved to the right by the IPPB control 156. As with the PEEP control mechanism, the amount that the shaft 130 moves to the right determines the pressure applied to the pressure plate 102.

If PEEP is desired intermittently, the PEEP control 146 is merely held down when the IPPB control 156 is released, thereby maintaining a residual pressure on the pressure plate 102. The fitting 154 also serves as a pressure limit override if pressure greater than that set by the IPPB pressure control ring is desired. The nut 148 limits the override pressure. The IPPB pressure adjustment ring 158 can be either continuously adjustable or detented at, for example, 22 cm $H_2O$ (child) or 44 cm $H_2O$ (adult) pressure settings.

Returning to the embodiment shown in FIG. 3, it will be appreciated that continuous PEEP may be provided by including a locking mechanism (not shown) for the PEEP control 118. PEEP pressure would then always be maintained and inhalation pressure would then be superimposed on it by the inhalation control 110.

As shown in FIG. 3, the resuscitator unit shown includes means for vacuum assisted exhalation. For this purpose the front pressurization chamber 16 is connected by a bore 162 which extends to the exterior of the valve body 14 and which is closed by a knob 164 which is in the configuration of a Coanda effect-producing nut or knob. The Coanda knob 164 is connected by a suitable passage (not shown) to a valve (analogous to the purge valve 88) on the exterior of the device. Actuation of the valve connects the front pressurization chamber 16 to the bore 162. Pressurized gas from the front pressurization chamber 16 then rushes through the bore 162 and out the gap 166, from which, by the action of the Coanda effect, the gas follows the contours of the knob 164 before it exits the regulator through the piston apertures 76 and the check valve 48. The Coanda effect around the knob 164 creates an area of negative pressure in the interior of the valve which forcefully evacuates air from the patient's air passages via the mouthpiece 42 and the housing 12. It is to be understood that the mouthpiece 42 can be configured for attachment to a standard respirator mask, endotracheal tube, etc.

If pressurized oxygen is the gas entering at the inlet 24, it may be desirable to dilute it with outside air. This can be accomplished through a dilution assembly 200 shown in FIG. 3. This dilution assembly 200 replaces the end cap 54 of the basic regulator shown in FIG. 2.

The dilution assembly 200 comprises a generally circular end cap 202 having an annular flange 204 which engages the periphery of the regulator housing 12. A grate 206 having a plurality of holes 208 is rotated by means of a handle 210 extending through a slot 212 in the end cap 202. The rotation of the grate 206 selectively aligns or unaligns the grate holes 208 with holes 214 in a fixed circular plate 216 attached to the interior of the end cap 202 adjacent the grate 206. The alignment of the grate holes 208 and the plate holes 214 determines how much air can be drawn through one or more holes 218 in the end cap 202. The holes 208 and 214 may be aligned to varying degrees during inhalation to vary the amount of dilution of the pressurized oxygen by ambient air. The injection nozzle effect produced at the gas outlet 22 creates the reduced pressure necessary to draw diluting air through the holes 218, 208, and 214 and past a resilient one-way inlet check valve 220 (which closes to prevent exhalation through the dilution assembly) into the interior of the regulator, where it is conducted into the mouthpiece 42 and into the air passages of the patient or user. During exhalation, the resilient inlet check valve 220 blocks the path of exhaled gas so that it cannot escape through the dilution assembly 200.

The dilution assembly 200 also includes a tubular insert 222 which carries a circular spring bearing member 224 which bears against the spring 52 in the same manner as the end cap 54 does in the embodiment of FIG. 2. The tubular insert 222 is made to be slidable within the housing 12 for adjustment of the pressure on the spring 52. The insert 222 has one or more inlet apertures 225 to allow incoming ambient air to enter the interior of the regulator.

FIG. 6 illustrates a combination no-oxygen vent and overpressure relief valve which are advantageously used with the resuscitator embodiment of FIG. 3. As shown in FIG. 6, the no-oxygen vent/overpressure relief valve assembly 240 is fitted into one of the gas inlets 24 and extends to the exterior of the housing 12. The assembly 240 comprises a cylindrical body 242 which is sealingly fitted into an aperture 243 in the regulator housing 12 to provide an air-tight seal. The top of the body 242 is sealed with an annular cap 244 having a central aperture 246. A piston 248 is slidably journaled within the gas inlet 24 and has a circumferential groove 250 carrying on O-ring 252 to provide a sealing fit with the walls of the inlet 24. Integral with the piston 248 and extending upwardly from it is a shaft 254 which extends upward axially through the center of the valve body 242 and out the aperture 246 in the valve cap 244. Carried on the shaft 254 is a circular valve closure plate 256, the upper surface of which seats around a lower peripheral edge 258 of the cylindrical valve housing 242. Within the valve housing 242 an annular valve body 260 journals the shaft 254 through an integral cylindrical neck 262. To provide a sealing engagement between the shaft 254 and the valve neck 262, the shaft is provided with an O-ring 264 seated in a circumferential groove 266. The valve body is provided with a downwardly extending annular peripheral lip 268. A coil spring 270 is seated between the valve cap 244 and the valve body 260 axially surrounding the shaft 254. The spring 270 biases the valve body 260 downwardly until the lip 268 is urged against the top surface of the valve closure plate 256, which may be thought of as a valve seat.

In operation, the inlet 24 in which the piston 248 is inserted is pressurized by the introduction of gas to the other of the two gas inlets 24. This pressurization urges the piston 248 upwardly against the force of the spring 270 acting through the valve body 260 and the valve closure plate or seat 256. The upward motion of the piston 248 bears with it the shaft 254 and thus the closure plate or seat 256 and so the latter member engages the peripheral edge 258 of the valve housing 242. The spring 270 urges the valve body 260 downwardly as previously mentioned until the valve body lip 268 seats against the valve seat 256. In this configuration the assembly 240 seals the interior of the regulator housing 12 from the exterior.

If there is insufficient oxygen pressure to push the piston 248 upwardly against the force of the spring 270, then the piston drops downwardly in the gas inlet 24 carrying the valve seat 256 downwardly, and outside air is allowed to enter the interior of the regulator through ports 272 in the side walls of the valve housing 242. Thus, if the patient is breathing through a sealed mask or endotracheal tube while unattended, this feature will prevent suffocation in the event of oxygen depletion or failure of the oxygen pressurization system.

Referring once again to FIG. 3, the resuscitator control system there illustrated is inherently incapable of imposing a pressure greater than 50 cm $H_2O$ (80 cm $H_2O$ maximum override pressure) on the patient's air passages, since the pressure plate 102 will be pushed against the spring 104 at or below that pressure which allows the excess pressure to bleed off past the resilient outlet check valve 48. Continuous air flow can only be present if the entire piston assembly or the valve spool 28 is stuck in the "valve open" position.

In the unlikely event that the main valve 28 is stuck open and the plate 102 is stuck, holding the outlet valve 48 closed, the safety assembly 240 of FIG. 6 also provides for overpressure relief. If the interior pressure in the regulator exceeds 50 cm $H_2O$, the excess pressure is communicated to the valve body 260 through one or more ports 274 in the valve seat 256. This excess pressure urges the valve body 260 away from the valve seat 256 against the force of the spring 270, thereby providing an escape path for the excess pressure through the ports 274 and 272.

Figure 9:
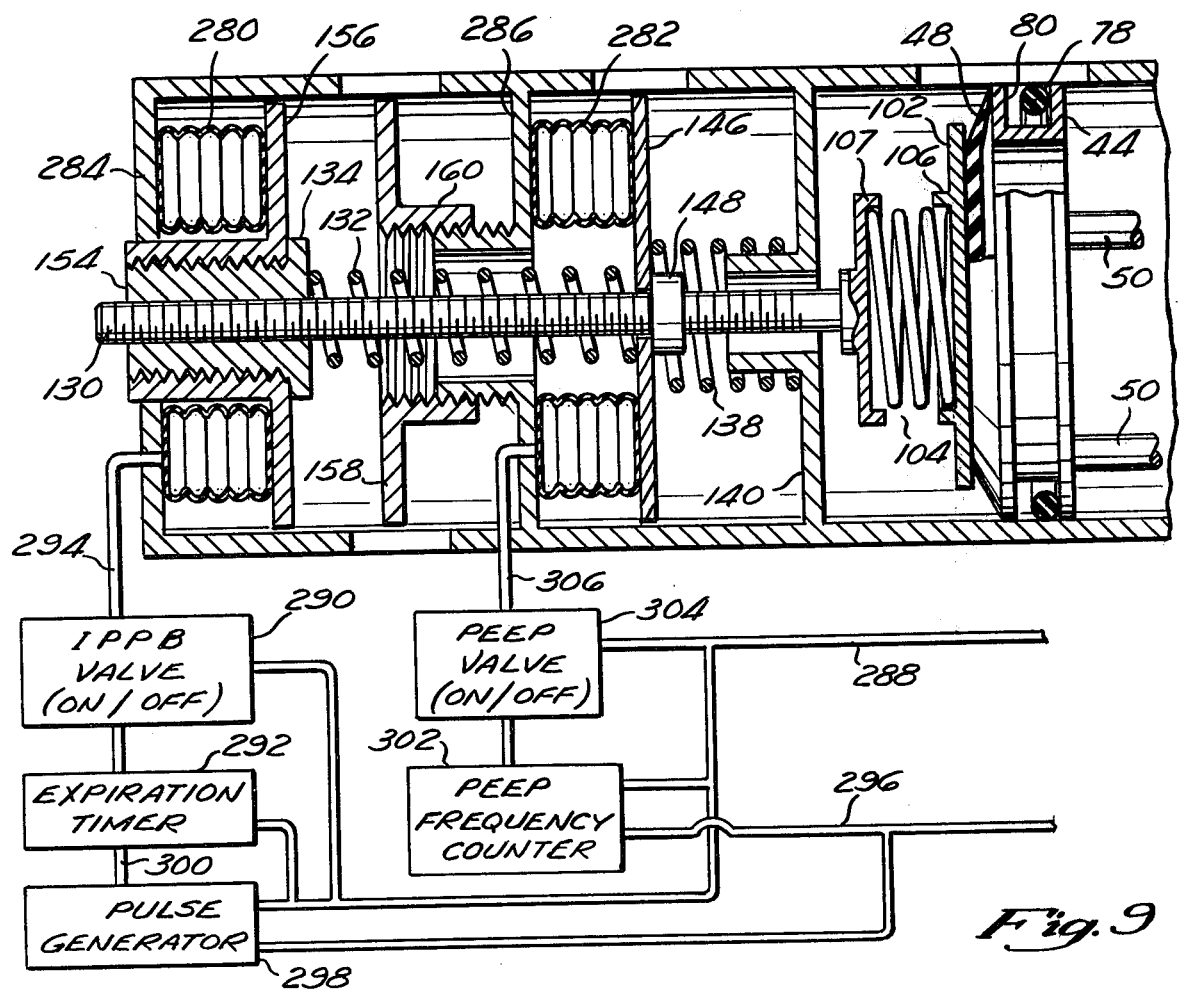
FIG. 9 is a diagramatic illustration of an automatic control system for the resuscitator embodiment of the invention.

The IPPB and PEEP controls of FIG. 8 can be automated with pneumatic controls. These controls can be either remote or incorporated in the valve assembly. FIG. 9 depicts the automatic operation of these controls.

In FIG. 9 the controls are essentially the same as in FIG. 8 with the primary difference being addition of a pair of annular aneroid bellows 280 and 282 for actuating the IPPB control 156 and the PEEP control 146, respectively. The IPPB bellows 280 is carried between a fixed annular plate 284 and the IPPB control lever 156 while the PEEP bellows 282 is carried between a second annular wall 286 and the PEEP control lever 146. Pressurized gas is led via a pipe 288 from the pressurized gas fitting 27 (FIG. 1) to an IPPB aneroid bellows inflation valve 290 and a timer 292 which opens the inflation valve 290 at set time intervals. When the IPPB valve 290 is opened, gas from the pipe 288 is fed into the IPPB aneroid bellows 280 from the valve 290 via a pipe 294. The bellows 280 then fills and expands, pushing the IPPB control lever 156 to the right, thereby pushing the shaft 130 to the right so that the pressure plate 102 is brought to bear against the piston 44, urging the piston to the right and initiating the inspiration flow as previously described. When the pressure in the patient's air passages rises high enough to balance the pressure on the spring 104, inspiration flow ceases, as previously described, and inspiration pressure drops to the pressure in the patient's air passages. A second pipe 296 transmits the inspiration pressure from the interior of the pressurized gas outlet 22 to a pulse generator 298 which senses the drop in inspiration pressure and sends a pneumatic pulse to the timer 292 through a pipe 300. This pulse resets the timer 292 so as to close the IPPB valve 290 which then vents to atmosphere, allowing the IPPB actuation bellows 280 to contract. When this happens, the springs 132 and 138 move the entire control assembly to the left, lifting the pressure plate 102 from the piston, thereby permitting unrestricted exhalation to atmosphere as previously described.

The inspiration pressure pipe 296 also transmits the inspiration pressure from the outlet 22 to a frequency counter 302 which cycles each time inspiration pressure rises in the pipe 296 and turns a PEEP valve 304 on or off in a selectable sequence. When the PEEP valve 304 turns on, it transmits pressurized gas from the pressurized gas line 288 to the PEEP actuation bellows 282 via a pipe 306. The expansion of the PEEP bellows 282 pushes the PEEP nut 148, the shaft 130, and ultimately the pressure plate 102 to the right against the piston 44. Exhalation effort increases the air passage pressure in the patient slightly above the set PEEP pressure, and the pressure plate 102 moves away from the piston 48, permitting exhalation to occur until the air pressure passage drops to the set PEEP pressure. The pressure plate 102 then again moves against the piston 44 and the air passage pressure is maintained at the set PEEP pressure.

The Industrial Respirator/Process Control Valve

Figure 10:
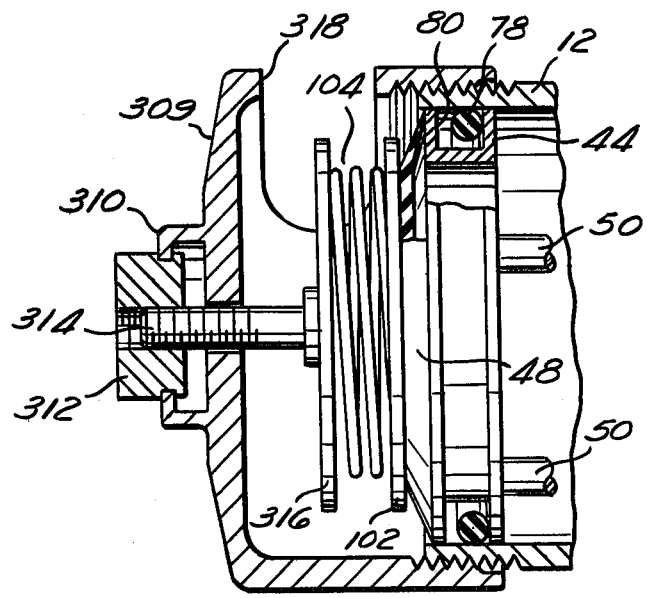
FIG. 10 is a fragmentary cross-sectional view showing a slightly modified form of the basic breathing regulator for use in a contaminated air environment.

FIG. 10 shows a modification of the basic respirator valve for use in contaminated gaseous environments. It is basically the scuba version of FIG. 2, but it may have the PEEP pressure controls shown in FIGS. 8 or 9. In this case the PEEP control would maintain a slight positive pressure in the face mask and the user's air passages to prevent the entrance of contaminated outside air if leaks in the mask system should develop.

In this embodiment, an end cap 309 is provided with an annular captured nut retainer 310 which retains a captured nut pressure control 312. The captured nut pressure control 312 is attached to shaft 314 which extends through the end cap 309, terminating in an outer spring pressure plate 316. The outer spring pressure plate 316 bears on the pressure control spring 104 which in turn bears against the piston pressure plate 102 as in the previously described embodiments. The pressure control nut 312 can thus be used to adjust the pressure applied to the piston 44 through the pressure plate 102 to control the positive pressure applied to the interior of the user's breathing mask through the regulator. In this manner, a continuous positive pressure can be provided in the mask and in the user's air passages even if leaks develop in the system. This is in contrast to present contaminated air breathing systems which depend either on a constant flow of pressurized breathing gas to overcome the effects of possible leakage or on spring pressure on an inhalation diaphragm and a heavier spring on the exhalation valve.

The mechanism illustrated in FIG. 10 may also be used as an industrial process control valve. When pressure is applied to the piston 44 by the pressure plate 102, a drop in pressure in the interior of the regulator opens the valve in the manner previously derscribed and pressurized gas flows into the interior of the valve until the pressure set by the pressure plate 102 is again reached. If there is a rise in pressure in the interior of the regulator, the pressure applied by the pressure plate 102 is overcome and the gas is allowed to escape through the piston ports 76 and past the check valve 48 in the manner previously described until the set pressure is again reached. In control terms, the valve is operating as a "high-low proportional set-point controller". The make up gas or overpressure relief flow rates are proportionately larger as the system pressure is further below or above the set pressure point.

In this application, an opening 318 in the end cap 309 is used as an overpressure relief outlet and it may be connected into a system so that the regulator operates as an inline controller with flow normally through the valve. The regulator would then serve to maintain upstream pressure by supplying make up gas if upstream pressure drops and by blocking flow if downstream pressure falls. The make up gas can be piped from the regulator and introduced into another part of the system.

Although the regulator has been described as being used with a gas, it is to be understood that in the industrial process control application, the regulator can be adapted for use with any fluid whether liquid, gas or a combination of the two.

High Altitude Breathing Regulator

Figure 7:
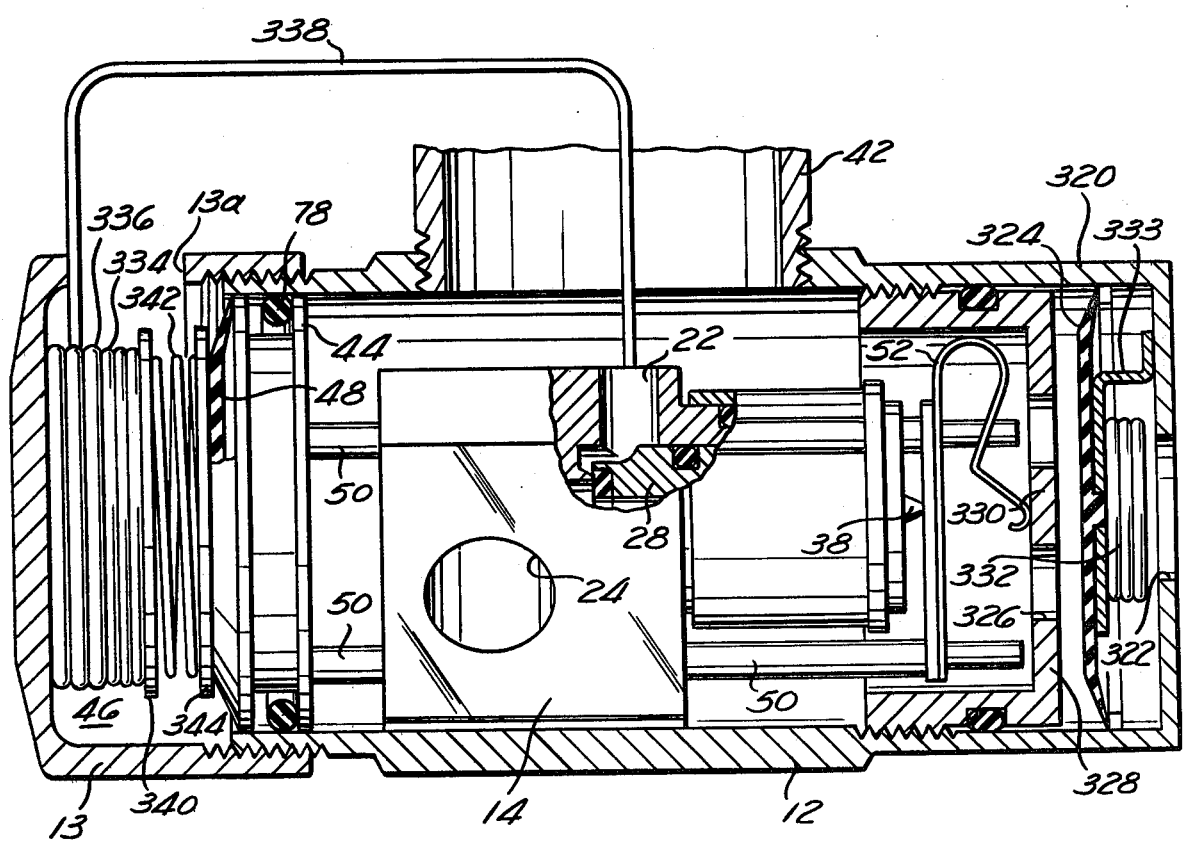
FIG. 7 is a cross-sectional view of a third embodiment of the present invention adapted for use as a high altitude breathing regulator.

The basic regulator can be adapted as shown in FIG. 7 for use as a mask-mounted breathing regulator for ascents from sea level to the highest altitude possible without external pressurization.

In this embodiment, the end cap 54 would be replaced by a vent cap 320 having an ambient air inlet vent 322. At low altitudes breathing would be through the ambient air inlet vent 322 past an inlet check valve 324 and into the interior of the device through one or more apertures 326 in a fixed grating 328. The grate 328 is provided with a central disk 330 against which the pilot closure spring 52 bears.

As altitude increases, an aneroid bellows 332, mounted on a bracket 333 located between the check valve 324 and the inlet 322, gradually expands in response to the diminishing ambient pressure until it completely seals the inlet vent 322. Thus, as the altitude increases and the ambient pressure drops, the bellows 332 would gradually occlude the vent 322 until the inhalation of the user reduces the pressure in the interior of the regulator sufficiently to open the main valve spool 28 as previously described so that pressurized oxygen is introduced into the mouthpiece 42 from the pressurized gas outlet 22. In this manner, the gas breathed by the user would gradually change from ambient air to pure pressurized oxygen as the user's altitude increased.

As shown in FIG. 7, the regulator has been adapted for pressurized breathing at high altitudes. A second sealed aneroid bellows 334 is contained within the chamber 46 in the end cap 13. The chamber 46, as previously described, is open to ambient through the opening 13a. Thus with increasing altitude the bellows 334 will gradually expand. An expandable bellows 336 is located between the second aneroid bellows 334 and the end cap 13. The interior of the expandable bellows 336 communicates with the pressurized gas outlet 22 through a conduit 338 so that, when the user inhales, a portion of the pressurized gas from the outlet 22 is directed into the expandable bellows 336 so that this bellows expands. It should be noted that the expandable bellows 336 is fully expanded in response to the user's inhalation pressure at the outlet 22, while the aneroid bellows 334 gradually expands in response to increasing altitude. The expansion of the two bellows 336 and 334 urges a plate 340 to the right so as to compress a spring 342. The spring 342 in turn bears against a pressure plate 344, which, as in the previously described embodiments, urges the piston 44 to the right to open the pilot orifice 36 and the main valve 28. The valve mechanism stays open, allowing pressurized gas to enter to user's air passages until the inhalation pressure in the user's passages is sufficient to overcome the force exerted on the pressure plate 344. This force remains constant with the altitude since the force exerted by the spring 342 is determined by the amount of expansion of the aneroid bellows 334, which in turn is directly proportional to decreasing ambient pressure with increasing altitude. Thus, the force exerted on the plate 344 by the spring 342 increases to compensate more or less exactly for the decreasing force exerted on the plate 344 by ambient air pressure keeping the total force on the pressure plate 344 more or less constant with increasing altitude (or decreasing ambient pressure). In this manner, positive pressure inhalation may be initiated at a predetermined altitude, with the level of inspiratory pressure necessary to overcome the force of the spring 342 being a a pressure level above ambient (gauge pressure) which gradually increases relative to the ambient pressure as altitude increases. Thus, the mechanism described maintains a substantially constant level of positive pressure breathing, which would otherwise decrease with increasing altitude due to decreasing ambient pressure against the external side of the piston 44.

Once the user's inspiratory pressure overcomes the force exerted by the spring 342, inspiration flow throughthe outlet port 22 ceases, as previously described in connection with the medical respirator embodiment. When inspiration ceases, the bellows 336 is depressurized through the conduit 338 and contracts, allowing the spring 342 to lift the pressure plate 344 from against the piston 44, thereby allowing substantially free flow exhalation to ambient pressure through the piston outlet apertures 76, as previously described, without any effort other than the minimal amount necessary to open the resilient outlet check valve 48. As in the medical respirator embodiment previously described, it will be appreciated that the pressure plate 344 which urges the piston 44 to the right automatically seals the exhalation path during inhalation by closing the outlet check valve 48 against the piston apertures 76.

The high altitude breathing regulator above described is small enough so that it may be mounted on the user's breathing mask, as opposed to present high altitude breathing regulators which are typically mounted in a control panel in the aircraft. The mask mounting of the unit provides a significant advantage especially during emergency bail out, since the unit can function with a small portable oxygen tank as the source of pressurized gas rather than the relatively large oxygen supplies needed with present emergency bail out systems which require a slow, continuous flow of oxygen.

The substantially effortless, free flow exhalation to ambient pressure described above, provides a further advantage in minimizing the probability of lung damage resulting from an explosive decompression in a pressurized cockpit. In such a situation, the sudden removal of pressure in the exterior of the avaitor's lungs causes the air within the lungs to expand very rapidly. Unless the air can rapidly escape through the aviator's air passages, this rapid expansion can cause massive rupturing of the lungs, a result which can be fatal. Typical aviator's breathing regulators, at present, require forceful exhalation to open the exhalation outlet. Thus, they are inherently slow acting, with the possibility of fatal consequences in the event of explosive decompression. In the present invention, on the other hand, the path of least resistance for the expanding air in the aviator's breathing passages is through the regulator directly to ambient, thus substantially minimizing the probability of lung rupture.

What is claimed is:

1. A device for the regulation of a user's breathing from a source of pressurized gas, comprising:
    a housing having passage means for conducting said pressurized gas to said user;
    a valve body in said housing, said valve body having a pressurized gas inlet and a gas outlet, said outlet communicating with said passage means;
    a first pressurization chamber in said body, communicating with said inlet;
    valving means, moveable within said body, for controllably opening and closing said outlet, said valving means having first and second surfaces, said first surface confronting said first chamber, said second surface having a larger area than said first surface;
    a second pressurization chamber communicating with said first pressurization chamber, said second surface of said valving means confronting said second chamber, said valving means being moveable in opposite directions within said body in response to the force differential between said first and second surfaces so that said valving means closes said gas outlet when the force on said second surface, equal to the pressure on said second surface times the area of said second surface, is greater than the force on said first surface, equal to the pressure on said first surface times the area of said first surface, thus closing said gas outlet when the pressures in said first and second pressurization chambers are equal, and said valving means opens said gas outlet when the force on said first surface is greater than the force on said second surface;

a pilot valve having pilot passage means for venting gas from said second chamber to reduce the pressure in said second chamber with respect to the pressure in said first chamber so that said valving means opens said outlet;

pilot passage closure means, slideably moveable between a first position and a second position, for closing said pilot passage means in said first position and opening said pilot passage means in said second position;

pilot valve actuating means, attached to said pilot passage closure means, and forming a pressure interface between the interior and exterior of said housing, for moving said closure means from said first position to said second position in response to an inhalation-induced reduction in pressure on the interior side of said interface with respect to the pressure on the exterior side of said interface; and exhalation outlet means from said housing.

2. The device of claim 1, wherein said pilot valve actuating means comprises:
a piston which is moveable within said housing; and
means for providing a substantially frictionless seal between said piston and said housing.

3. The device in claim 1, further comprising:
means for adjustably diluting said pressurized gas in said passage means with ambient air from the atmosphere external to said housing.

4. The device of claim 3, wherein said diluting means comprises:
an air inlet into said housing;
a fixed apertured member in said housing; and
means for variably obstructing the flow of air from said air inlet through said apertured member.

5. The device of claim 4, wherein said variable flow obstructing means comprises:
a moveable apertured member connected to said housing and located between said fixed apertured member and said air inlet.

6. The device of claim 4, wherein said variable flow obstructing means comprises:
aneroid means in said housing proximate said air inlet, for expanding to increasingly obstruct said air inlet in response to decreasing ambient pressure.

7. The device of claim 1, further comprising:
an air inlet into said housing; and
automatic valving means for closing said air inlet when said pressurized gas in said pressurized gas inlet is at or above a first predetermined pressure and opening said air inlet when the pressure of said pressurized gas in said pressurized gas inlet is below said first predetermined pressure.

8. The device of claim 7, wherein said automatic valving means additionally opens said air inlet when the pressure of said pressurized gas in said passage means is at or above a second predetermined pressure, so that said air inlet provides an over-pressure relief outlet.

9. The device of claim 1, wherein said pilot valve actuating means moves said closure means from said second position to said first position in response to an increase in pressure on the interior side of said pressure interface with respect to the pressure on the exterior side of said interface.

10. The device of claim 9, further comprising:
breathing pressure adjustment means, acting on said pilot valve actuating means for both (a) providing positive pressure breathing by said user during inhalation, and (b) maintaining a predetermined positive and expiratory pressure is provided.

11. The device of claim 10, wherein said breathing pressure adjustment means comprises:
pressurization means engageable with the exterior side of said pressure interface, for controllably applying a presure to said interface to vary said pressure on the interior side of said pressure interface which causes said pilot passage closure means to move between said second position and said first position.

12. The device of claim 11, wherein said exhalation outlet means is through said pressure interface, and said pressurization means closes said exhalation outlet means during inhalation.

13. The device of claim 11, further comprising:
means, responsive to the pressure at said gas outlet for controllably engaging said pressurization means against the exterior side of said pressure interface.

14. The device of claim 9, further comprising:
pressurized inhalation means for providing positive pressure inhalation at a constant absolute pressure level relative to decreasing ambient pressure.

15. The device of claim 14, wherein said pressurized inhalation means comprises:
pressure-responsive means for increasing said predetermined pressure which cause said pilot passage closure means to move between said second position and said first position as said ambient pressure decreases.

16. The device of claim 15, wherein said pressure-responsive means comprises:
first expandable means for expanding in response to said user's inhalation; and
second expandable means for gradually expanding in response to decreasing ambient pressure, the expansion of said first and second expandable means pressurizing the external side of said pressure interface.

17. The device of claim 1, further comprising:
means on said valve body and in communication with said pressurized gas inlet, for providing vacuum assisted exhalation using the Coanda effect.

18. A device for regulating a user's breathing from a source of pressurized gas, comprising:
a housing having passage means for conducting said pressurized gas to said user;
a valve body in said housing and having an inlet and an outlet for said pressurized gas, said outlet communicating with said passage means;
main valving means moveable within said valve body, for opening and closing said outlet;
pilot valving means, slideably moveable between an open and a closed position, for controllably actuating said main valving means against the force of said pressurized gas;
pressure-responsive means, attached to the low pressure side of said pilot valving means and providing a pressure interface between the interior and exterior of said housing, for moving said pilot valving means to said open position when the pressure on the interior side of said interface drops below the pressure on the exterior side of said interface by a first predetermined amount;

means for moving said pilot valving means to said closed position when the pressure on the interior side of said pressure interface rises by a second predetermined amount in response to an increase in pressure in said passage means as a result of the end of inhalation; and pressurization means, engageable with the exterior side of said pressure interface, for adjutably applying a pressure to said exterior side to vary said second predetermined amount of pressure.

19. The device of claim 18, additionally comprising:

breathing pressure adjustment means, acting on said pressure-responsive means, for selectably (a) providing positive pressure inhalation, and (b) maintaining a predetermined positive pressure in said passage means so that positive end expiratory pressure is provided.

20. The device of claim 19, wherein said breathing pressure adjustment means comprises:

means for independently controlling the pressure of said positive pressure breathing and said predetermined positive pressure at the end of exhalation.

21. The device of claim 19, wherein said pressurization means further comprises:

aneroid means, responsive to the pressure of said pressurized gas and the pressure at said outlet, for controllably actuating said breathing pressure adjustment means.

22. The device of claim 18, wherein said pressurization means comprises:

pressurized inhalation means for providing positive pressure inhalation at a constant absolute pressure level relative to decreasing ambient pressure.

23. The device of claim 22, wherein said pressurized inhalation means comprises:

aneroid means for increasing said second predetermined pressure with decreasing ambient pressure.

24. The device of claim 23, wherein said aneroid means comprises:

first aneroid means for expanding in response to said user's inhalation; and second aneroid means for gradually expanding in response to decreasing ambient pressure, the expansion of said first and second aneroid means applying a pressure to the exterior side of said pressure interface to vary said second predetermined pressure.

25. The device of claim 18, further comprising:

rigid connecting means for attaching said pressure-responsive means to said pilot valving means to provide unitary, straight-line motion of said pilot valving means and said pressure-responsive means.

26. The device of claim 18, further comprising:

means responsive to the ambient pressure external to said housing and acting on said main valving means, for varying the amount which said pressurized gas outlet is opened by said main valving means in response to changes in said ambient pressure.

27. The device of claim 18, wherein said main valving means comprises:

a pressurized gas outlet occluding portion; and means for generating a partial pressure recovery proximate said occluding portion when said pressurized gas flows through said outlet past said main valving means as said main valving means opens said outlet, so that the fluttering of said main valving means is substantially eliminated.

28. In a device for the regulation of a user's breathing from a source of pressurized gas, of the type having a housing which includes a passage for conducting said pressurized gas from said source to said user, said passage comprising a main valve, moveable within said housing, for regulating the flow of said pressurized gas, and a pilot valve orifice for controlling movement of said main valve against the force exerted by said pressurized gas, the improvement comprising:

pilot valve closure means movable in a straight line path for selectively blocking said orifice;

pressure-responsive means in said housing for actuating by straight-line motion said pilot valve closure means; and pressurization means, selectably acting on said pressure-responsive means, for (a) effecting positive pressure breathing during inhalation, and (b) maintaining a predetermined positive pressure in said user's air passages at the end of exhalation, so that positive end expiratory pressure is provided.

29. The device of claim 28, wherein said pressure-responsive means comprises:

a piston providing a pressure interface between the interior and exterior of said housing and moveable from a first position to a second position within said housing when the pressure on the exterior side of said pressure interface exceeds the pressure on the interior side of said pressure interface by a predetermined amount;

means engaging said pilot valve closure means for closing said pilot valve orifice when the pressure differential from the exterior side to the interior side of said pressure interface is less than said predtermined amount; and connecting means for rigidly connecting said piston and said pilot valve closure means for closing said pilot valve orifice when the pressure differential from the exterior side to the interior side of said pressure interface is less than said predetermined amount so that the movement of said piston from said first position to said second position opens said pilot valve closure means, and the closing of said pilot valve orifice by said pilot valve closure means moves said piston from said second position to said first position.

30. The device of claim 29, further comprising:

sealing means for providing a substantially frictionless seal between said piston and said housing as said piston moves between said first and second positions; and outlet means for permitting exhalation through said pressure interface.

31. The device of claim 30, wherein said outlet means comprises:

an aperture in said pressure interface; and resilient valving means for sealing said aperture during inhalation and opening said aperture during exhalation.

32. The device of claim 29, wherein said pressurization means comprises:

means for adjustably exerting a pressure on the exterior side of said pressure interface.

33. The device of claim 29, wherein said pressurization means comprises:

pressure adjustment means for adjustably increasing the pressure on the exterior side of said pressure interface during inhalation to increase the pressure required on the interior side of said pressure interface to close said pilot valve closure means.

34. The device of claim 33, wherein said pressurization means further comprises:
second pressure adjustment means for adjustably applying pressure to the exterior side of said pressure interface during exhalation to cause said piston to move from said first to said second position when the difference between said applied pressure and said user's expiratory pressure is greater than said predetermined pressure differential, so that said pilot valve closure means is opened.

35. A device for regulating a user's breathing from a source of pressurized gas comprising:
a housing having passage means for conducting said pressurized gas to said user;
a valve body in said housing and having inlet and outlet means for said pressurized gas, said outlet means communicating with said passage means;
pressurized gas valving means, moveable between a firs and a second position in said valve body, for respectively closing and opening said outlet means;
pressure responsive means, including a pressure interface between the interior and exterior of said housing for both (a) moving said pressurized gas valving means between said first and second positions in response to said user's inhalation, and (b) providing an exhalation outlet from said housing in response to said user's exhalation;
means for maintaining said exhalation outlet closed when the pressure in the interior of said housing is below a specified pressure; and
means for adjustably applying pressure to said pressure interface on the side exterior of said housing to adjust said specified pressure required to open said exhalation outlet.

36. The device of claim 35, wherein said pressure responsive means comprises:
a piston having an exterior side and an interior side to provide said pressure interface, and moveable within said housing in a first direction to move said pressurized gas valving means from said first position to said second position.

37. The device of claim 36, wherein said pressure-responsive means further comprises:
means for moving said pressurized gas valving means from said second position to said first position in response to a predetermined inspiratory pressure in said user's breathing passges, the movement of said pressurized gas valving means from said second position to said first position urging said piston toward a second direction, opposite to said first direction, against a pressure on the exterior side ofsaid piston.

38. The device of claim 37, wherein said means for adjustably applying pressure comprises:
means acting on the exterior side of said piston, for adjusting said predetermined inspiratory pressure.

39. The device of claim 38, wherein said means acting on the exterior side of said piston comprises:
pressurization means, engageable with the exterior side of said piston, for adjustably biasing said piston toward said first direction, so that said predetermined inspiratory pressure which causes said pressurized gas valving means to move from second position to said first position is adjustably varied.

40. The device of claim 39, wherein said pressurization means comprises:
first means for providing positively pressurized inhalation by engaging said piston during inhalation; and
second means for maintaining a predetermined positive pressure in said user's breathing passage at the end of exhalation, so that positive end expiratory pressure is provided.

41. the device of claim 40, wherein said first and second means are independently operable.

42. The device of claim 38, wherein said pressure adjustment means increases said predetermined inspiratory pressure relative to ambient pressure in response to decreasing ambient pressure on the exterior of said housing.

43. The device of claim 42, wherein said pressure-adjustment means comprises:
first expandable means for expanding in response to said user's inhalation;
second expandable means for gradually expanding in response to decreasing ambient pressure on the exterior of said housing; and
said first and second expandable means and said piston being arranged so that the expansion of said first and second expandable means increasingly pressurizes the exterior side of said piston in proportion to the decrease in ambient pressure on the exterior of said housing, to maintain a substantially constant absolute pressure on the exterior side of said piston, so that said predetermined inspiratory pressure which causes said pressurized gas valving means to move from said second position to said first position is increased relative to decreasing ambient pressure.

44. The device of claim 36, wherein said exhalation outlet is provided through said piston, and said pressure-responsive means comprises:
exhalation valving means for opening said exhalation outlet only when said pressurized gas valving means is in said first position.

45. The device of claim 36, further comprising:
substantially frictionless sealing means between said piston and said housing.

46. The device of claim 35, wherein said pressure-responsive means comprises:
aperture means through said pressure interface; and
means for closing said aperture means during inhalation and opening said aperture means in response to said user's exhalation to provide said exhalation outlet.

47. The device of claim 35, wherein said pressurized gas valving means comprises:
a main valving means for opening and closing said pressurized gas outlet means; and
pilot valving means for actuating said main valving means against the force exerted by said pressurized gas.

48. The device of claim 47, wherein said pressure-responsive means is rigidly linked to said pilot valving means, and said pressure-responsive means is moveable in a first direction in response to inhalation to open said pilot valving means, thereby opening said main valving means.

49. The device of claim 47, wherein said main valving means comprises:

a slidable member in said valve body and having first and second surfaces, said member being slidable in a first direction to open said pressurized gas outlet means when the force exerted by said pressurized gas on said first surface exceeds the force exerted by said pressurized gas on said second surface, the opening of said pressurized gas outlet means tending to cause a sudden decrease in the gas pressure proximate said first surface, resulting in a corresponding decrease in the force exerted by said pressurized gas against said first surface; and means, proximate said first surface, for recovering at least part of the gas pressure proximate said first surface to maintain a force against said first surface as said pressurized gas outlet means is opened so that the chattering of said main valving means is substantially prevented.

50. The device of claim 35, further comprising:
an air inlet into said housing; and
automatic valving means for closing said inlet when said pressurized gas in said pressurized gas inlet means is at or above a first predetermined pressure, and opening said air inlet (a) when the pressure of said pressurized gas in said inlet means is below said first predetermined pressure, and (b) when the pressure in said housing is above a second predetermined pressure.

51. The device of claim 35, wherein said valve body outlet means provides a jet nozzle effect to reduce inhalation effort.

52. A device for regulating the flow of a pressurized fluid, comprising:
a housing having a passage means for conducting said pressurized fluid to a point of use;
a valve body in said housing, said valve body having an inlet and an outlet for said pressurized fluid, said inlet adapted to be connected to a pressurized fluid source, said outlet communicating with said passage means in said housing;
main valving means in said valve body for opening and closing said outlet, said valving means having two opposed sides, the pressure of said pressurized fluid tending to maintain a greater fluid pressure force on one side of said main valving means than the fluid pressure force on the other side thereof to maintain said main valving means in a first position which closes said outlet;
linearly movable pilot valving means for controllably venting the pressure which maintains said main valving means in said first position, so that said main valving means moves to a second position which opens said outlet; and pressure-responsive means, including a pressure interface between the interior and exterior of said housing for both (a) actuating said pilot valving means when the pressure on the interior side of said pressure interface is less than the pressure on the exterior by a predetermined amount and (b) providing exhaust outlet means for said fluid to exit said housing when said main valving means is in said first position.

53. The device of claim 52, wherein said pressure-responsive means comprises:
a piston having an exterior side and an interior side to provide said pressure interface, said piston being connected to said pilot valving means and moveable within said housing in a first direction to open said pilot valving means.

54. The device of claim 53, wherein said pressure-responsive means further comprises:
means for closing said pilot valving means in response to a predetermined increase in pressure in said housing, said main valving means moving from said second position to said first position to close said pressurized fluid outlet in response to the closing of said pilot valving means, the closing of said pilot valving means urging said piston toward a second direction opposite to said first direction, against a pressure on the exterior side of said piston.

55. The device of claim 54, further comprising:
pressure adjustment means, acting on the exterior side of said piston, for adjusting said predetermined increase in pressure which actuates said pilot valve closing means.

56. The device of claim 55, wherein said pressure-adjustment means comprises:
pressurization means, engageable with the exterior side of said piston, for adjustably biasing said piston toward said first direction, so that said predetermined increase in pressure which actuates said pilot valve is adjustably varied.

57. The device of claim 56, wherein said pressurized fluid is a breathable gas, said housing includes passage means for communication with a user's breathing passages, and said pressurization means comprises:
breathing pressure control means for adjustably controlling said user's inhalation effort and exhalation effort.

58. The device of claim 57, wherein said breathing pressure control means comprises:
first means for controlling inspiratory pressure by biasing said piston in said first direction during inhalation; and
second means for adjustably maintaining a positive end expiratory pressure in said user's breathing passages by biasing said piston in said first direction at the end of exhalation.

59. The device of claim 58, wherein said first and second means are independently operable.

60. The device of claim 59, further comprising:
said first expandable means for actuating said first means by expanding to engage said first means;
first valving means for admitting said breathable gas into said first expandable means to effect the expansion thereof, and for venting said gas from said first expandable means;
timing means for actuating said first valving means to admit said gas to said first expandable means at a selected time interval;
first control means, responsive to said user's inspiratory pressure, for actuating said first valving means to vent said gas from said first expandable means when a predetermined inspiratory pressure is reached;
second expandable means for actuating said second means by expanding to engage said second means;
second valving means for admitting said breathable gas into said second expandable means to effect the expansion thereof, and for venting said gas from said second expandable means; and
second control means responsive to said inspiratory pressure, for actuating said second valving means to alternately admit and vent said gas in a selectable sequence, said sequence initiated in response to a predetermined rise in said inspiratory pressure.

61. The device of claim 57, wherein said pressurization means comprises:
expandable means, engaging the exterior side of said piston, for expanding in response to decreasing ambient pressure on the exterior side of said piston, said expansion and said decreasing ambient pressure maintaining a substantially constant total pressure on the exterior side of said piston to bias said piston in said first direction with substantially constant pressure as said ambient pressure decreases, so that said predetermined increase in pressure which actuates said pilot valve is correspondingly increased relative to decreasing ambient pressure.

62. The device of claim 53, wherein said exhaust outlet means is provided through said piston, and said pressure-responsive means comprises:
said exhaust outlet valving means opening said exhaust outlet means only when said pilot valving means is closed.

63. The device of claim 53, further comprising:
sealing means for providing a substantially frictionless seal between said piston and said housing.

64. The device of claim 63, wherein said sealing means comprises:
a groove around the periphery of said piston; and
an "O" ring of generally circular cross-section in said groove having a thickness less than both the depth and the width of said groove and a diameter slightly larger than the inside diameter of said housing around said piston to permit limited free movement of said piston.

65. The device of claim 63, wherein said sealing means comprises:
a sealing member mounted on said housing, sealingly engaging said piston at the extremes of its movement within said housing, but disengaging said piston during said movement.

66. The device of claim 53, wherein the movement of said piston in said first direction actuates said pilot valving means by straight line motion.

67. The device of claim 52, wherein said exhaust outlet means from said housing comprises:
means forming an aperture through said pressure interface; and
means for closing said aperture when the pressure on the interior side of said interface is less than or equal to the pressure on the exterior side of said interface, and opening said aperture when the pressure on the interior side of said interface exceeds the pressure on the exterior side.

68. the device of claim 52, further comprising:
means engageable against the exterior side of said pressure interface for adjustably increasing the pressure on said exterior side.

69. The device of claim 52, wherein said main valving means comprises:
a slidable member in said valve body and having first and second surfaces, the area of said second surface being greater than the area of said first surface, said member being slidable in a first direction to open said pressurized fluid outlet when the force exerted by said pressurized fluid on said first surface exceeds the force exerted by said pressurized fluid on said second surface, the opening of said pressurized fluid outlet tending to depressurize the area proximate said first surface resulting in a corresponding decrease in the force exerted on said first surface; and means proximate said first surface, for providing at least a partial fluid pressure recovery in said area proximate said first surface as said pressurized fluid outlet is opened to maintain a force against said first surface, so that said main valving means is substantially prevented from chattering.

70. A breathing regulator comprising:
a valve body having inlet means for communicating with a source of pressurized breathable gas, and gas outlet means for communicating with the breathing passages of an animal;
main valving means in said valve body for opening and closing said outlet means, said valving means, when closed, having a pair of unequal sized opposing surfaces subject to the pressure of said pressurized breathable gas to bias said valving means to a closed position;
pilot valving means for controllably actuating said main valving means against the pressure exerted by said pressurized gas; and
a piston rigidly attached to said pilot valving means for actuating said pilot valving means in response to a predetermined, breathing induced change in pressure in said outlet means.

71. A breathing regulator, comprising:
a valve body having inlet means for communicating with a source of pressurized breathable gas, and outlet means for said gas, said outlet means being fluidly connectable with the breathing passages of an animal;
main valving means, in said valve body, for opening and closing said outlet means;
a pilot valve chamber communicating with said main valving means, the pressure in said chamber controlling said opening and closing of said outlet means by said main valving means;
a pilot orifice in said pilot valve chamber for exhausting said chamber;
slideably movable pilot orifice closing means for controllably exhausting said chamber; and
linearly moveable, pressure-responsive means for actuating said orifice closing means in response to a predetermined change in pressure in said outlet means, said change in pressure being induced by said animal's breathing.

72. A device for the regulation of a user's breathing from a source of pressurized gas, comprising:
a valve body having inlet and outlet means for said pressurized gas;
an outlet chamber for communicating with said outlet means and said user's breathing passages;
valving means in said valve body for controllably opening and closing said outlet means in response to said user's inspiratory and expiratory pressures;
said inspiratory and expiratory pressures being determined by a pressure differential induced between the interior and exterior of said outlet chamber during inhalation and exhalation, respectively; and
means forming a pressure-responsive interface between the interior and exterior of said outlet chamber for controllably varying both said inspiratory and expiratory pressures by controllably adjusting said pressure differential.

73. The device of claim 72, further comprising:
means for substantially preventing damage to said user's lungs resulting from an explosive decompression of said user's environment.

74. A device for the regulation of a user's breathing from a source of pressurized gas, comprising:
- a valve body having pressurized gas inlet means and gas outlet means communicating with said user's breathing passages;
- valving means in said valve body for controllably opening said outlet means in response to said user's inhalation and closing said outlet means when a predetermined absolute inspiratory pressure is reached in said user's breathing passages and communicated to said gas outlet means, said predetermined absolute inspiratory pressure tending to remain constant with decreasing external ambient pressure; and
- means, responsive to the pressure at said gas outlet means and the external ambient pressure, for maintaining said predetermined inspiratory pressure as said ambient pressure decreases.

UNITED STATES PATENT AND TRADEMARK OFFICE
CERTIFICATE OF CORRECTION

PATENT NO. : 4,436,090
DATED : July 30, 1984
INVENTOR(S) : Philip H. Darling

It is certified that error appears in the above-identified patent and that said Letters Patent is hereby corrected as shown below:

Column 2, Line 68, "reuslts" should be --results--

Column 7, Line 25, symbol between "spool" and "to the right" should be deleted,--28-- should be inserted.

Column 8, Line 9, "29a" should be ---59a---.

Column 9, Line 29, "both" should be ---<u>both</u>---.

Column 9, Line 36, "direct" should be --<u>direct</u>--

Column 10, Line 22, "for" should be --from--.
Column 10, line 20, delete "and".
Column 20, Line 10, after "positive" insert --pressure in said passage means, so that positive end--.

Column 20, Line 15, "presure" should be --pressure--.

Column 23, Line 24, "firs" should be --first--.

Column 23, Line 57, "ofsaid" should be --of said--.

Column 24, Line 12, "the" should be --The--.

UNITED STATES PATENT AND TRADEMARK OFFICE
CERTIFICATE OF CORRECTION

PATENT NO. : 4,436,090
DATED : July 30, 1984
INVENTOR(S) : Philip H. Darling

Page 2 of 2

It is certified that error appears in the above-identified patent and that said Letters Patent is hereby corrected as shown below:

Column 27, Line 51, "the" should be --The--.

*Signed and Sealed this*

*Twenty-sixth* Day of *February 1985*

[SEAL]

*Attest:*

DONALD J. QUIGG

*Attesting Officer*     *Acting Commissioner of Patents and Trademarks*